United States Patent [19]
Mathiasen

[11] Patent Number: 5,980,506
[45] Date of Patent: Nov. 9, 1999

[54] SUBCUTANEOUS INFUSION DEVICE

[76] Inventor: Orla Mathiasen, 2, Åholmvej, Osted, DK-4000 Roskilde, Denmark

[21] Appl. No.: 09/045,480
[22] Filed: Mar. 20, 1998
[51] Int. Cl.⁶ .................................................. A61M 25/16
[52] U.S. Cl. ........................... 604/535; 604/533; 604/93; 604/905
[58] Field of Search ............................. 604/93, 115, 116, 604/164, 167, 169, 245, 246, 256, 264, 280, 283, 909, 533, 535

[56] References Cited

U.S. PATENT DOCUMENTS

| | | |
|---|---|---|
| 4,966,589 | 10/1990 | Kaufman .................................. 604/174 |
| 5,522,803 | 6/1996 | Teissen-Simony . |
| 5,545,143 | 8/1996 | Fischell . |

*Primary Examiner*—Wynn Wood Coggins
*Assistant Examiner*—Loan H. Thanh
*Attorney, Agent, or Firm*—Brinks Hofer Gilson & Lione

[57] ABSTRACT

The invention relates to a subcutaneous infusion device comprising a housing; a flow channel within the housing; a cannula extending from the housing and being in flow communication with the flow channel; a connector for delivery of fluid into the flow channel; a guide means for guiding the connector with the needle into a correct position in relation to the housing; a base part where the housing is mounted pivotably in relation to this base part. By incorporating the housing pivotably in relation to a base part it is possible to pivote the housing to an increased angle in relation to the skin surface and hereby facilitate the mounting of the connector in the housing since there is now more space present for performing this operation. Hereby the handling of the device has been simplified.

12 Claims, 7 Drawing Sheets

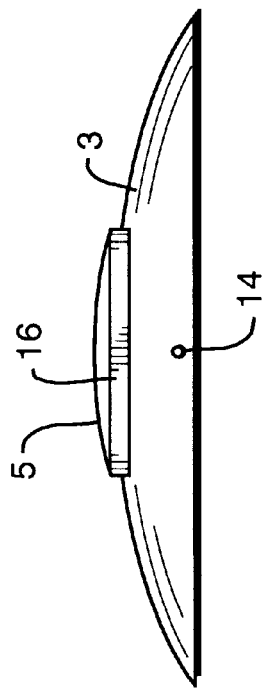
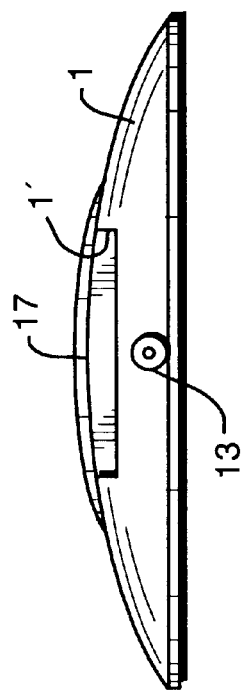

SUBCUTANEOUS INFUSION DEVICE

BACKGROUND OF THE INVENTION

The present invention relates to infusion devices for subcutaneous delivery of a medication or a therapeutic fluid by means of an external infusion system and more particularly to an infusion device having releasably connected means for delivery of the medication or the therapeutic fluid from the external infusion system.

Infusion devices are generally known in the art for delivering a medication or a therapeutic fluid to a subcutaneous site in a patient by means of a cannula inserted through the patients skin to the subcutaneous site. Such devices commonly comprise a tubular cannula extending from a housing adapted to receive the desired medication via disconnectable means for suitable connection to further components of the infusion system. The possibility of disconnecting the infusion set from the further parts of the infusion system is provided in order to improve the user comfort. The user is enabled to perform activities which do not allow the presence of a pump or the like, or which are hindered by the presence of a pump or the like. In the disconnected state only a part of the infusion set is worn by the patient. This allows for increased mobility. In order to provide such disconnectable means and still maintain a fluid-tight sealing towards the interior of the housing and the tubular cannula that prevents contamination of the infusion site, such devices are commonly provided with a self-sealing penetrable septum on either the housing or the disconnectable part and a hollow needle on the other part adapted to penetrate the septum. Upon withdrawal of the needle from the septum this provides a fluid-tight sealing towards the interior of the housing. The septum and the needle further provides a fluid-tight sealing between the housing and the connector means when medication or therapeutic fluid is delivered to the patient from the external infusion system. Subcutaneous infusion devices of this generally known type are known from e.g. U.S. Pat. No. 5,522,803 to Teissen-Simony and U.S. Pat. No. 5,545,143 to Fischell.

Due to the relatively small dimensions of such devices and due to the acute insertion angle in relation the skin surface the assembling of the housing and the connector is difficult as the fingers of the user get into close contact with the skin at the insertion site.

For these reasons there is a need for improvements in the infusion devices of the type mentioned in the foregoing, and particularly with respect to providing an infusion device which has improved properties of use and more particularly to an infusion device where the connector in a significant easier manner can be mounted on the housing of the infusion device. The infusion device according to the invention remedies the above mentioned disadvantages and provides further advantages which will become apparent from the following description.

SUMMARY OF THE INVENTION

According to the invention a subcutaneous infusion device has been developed wherein said subcutaneous infusion device comprises:
  a housing;
  a flow channel within the housing;
  a cannula extending from the housing and being in flow communication with the flow channel;
  a connector for delivery of fluid into the flow channel;
  a guide means for guiding the connector with the needle into a correct position in relation to the housing;
  where the guide means has incorporated means for interlocking the connector and the housing.

By incorporating the housing pivotably in relation to a base part it is possible to pivote the housing to an increased angle in relation to the skin surface and hereby facilitate the mounting of the connector in the housing since there is now more space present for performing this operation. Hereby the handling of the device has been simplified.

In a preferred embodiment the infusion device comprises a self-sealing septum covering the flow channel and a needle on the connector for penetrating the self-sealing septum covering the flow channel in the housing. This embodiment ensures a proper sealing of the housing and a proper delivery through the septum.

In one preferred embodiment the guide means comprises at least one elongate flexible element having a barb, and wherein the housing comprises a recess for receiving the elongate flexible element and an aperture for interacting with the barb on the elongate flexible element. In another preferred embodiment the guide means comprises two elongate flexible elements each having a barb, and wherein the housing comprises two recesses for receiving the elongate flexible elements and locking edges for interacting with the barb on each elongate flexible element.

In both embodiments it is a possibility that each of the elongate flexible elements comprises a bending area and a pivoting area mutually adapted to bring the barbs out of engagement upon effecting a pressure on the bending area hereby pivoting the outer end of each arm.

In a preferred embodiment each elongate flexible element is placed so as to cover the needle. Hereby harmful injuries caused by the needle are avoided to the widest possible extent.

In order to provide a guiding effect the housing can comprise grooves parallel with the bore and on the connector fins adapted for corresponding with the grooves. Another possibility comprises grooves in the connector parallel with the bore and on the housing fins adapted for corresponding with the grooves.

The infusion device according to the invention will in the following be explained more detailed with reference to the drawings showing a preferred embodiment.

BRIEF DESCRIPTION OF THE DRAWINGS

FIG. 7 is a rear end view of the housing of the device shown in FIG. 1;

FIG. 8 is a front end view of the connector of the device shown in FIG. 1;

DESCRIPTION OF THE PREFERRED EMBODIMENTS

Figure 1:
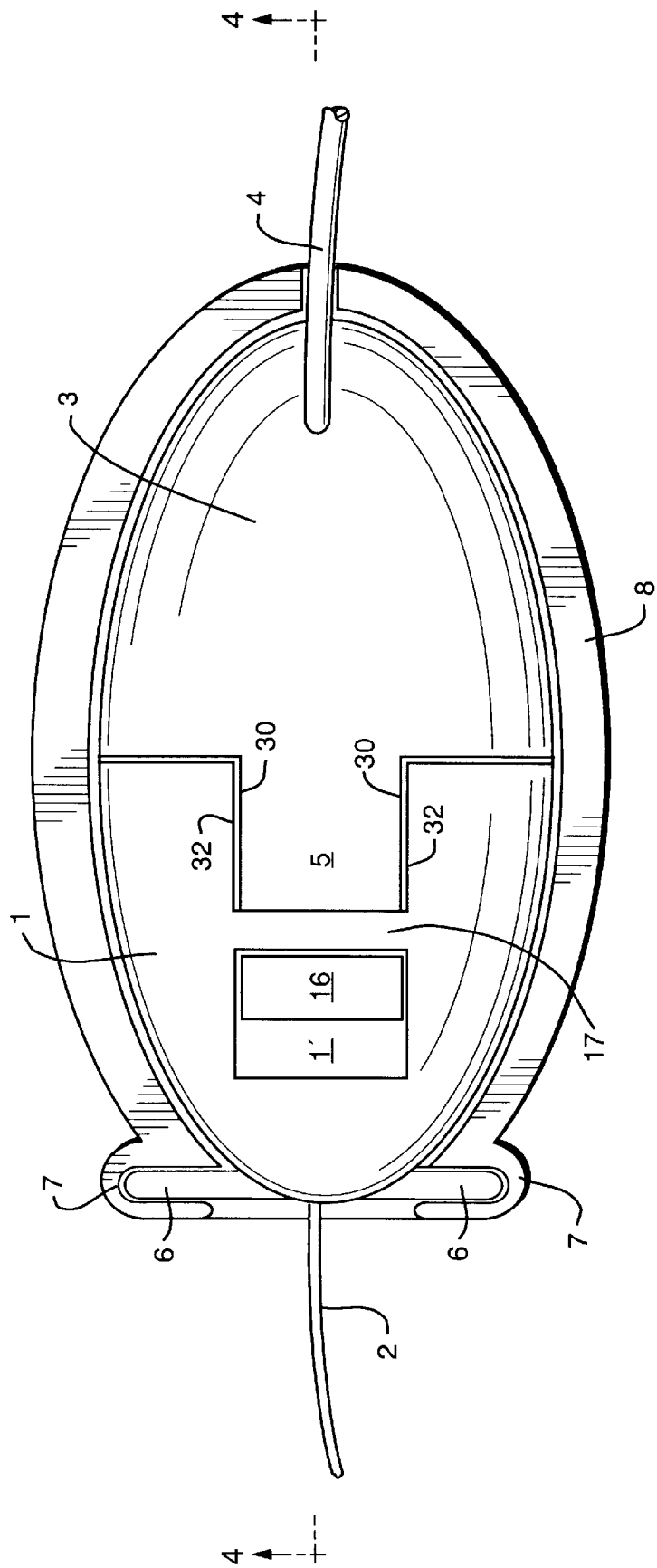
FIG. 1 is a top view of a preferred embodiment of the subcutaneous infusion device according to the invention.

It appears from FIG. 1 that the preferred embodiment of the infusion device comprises a housing 1 and a soft cannula 2 extending from the housing. A connector 3 is connected to the housing and a hose 4 extends from the connector for providing fluid communication between a pump (not shown) and the connector. It further appears that the device has a substantially elliptic ground shape. The device could however have any ground shape providing the bore, the self-sealing septum and the cannula in the housing and the bore, the hose 4 and a needle in the connector and furthermore the combined guide and locking means in connection with the housing and the connector. The housing 1 comprises at its foremost end shafts 6 adapted to interact pivotably with grooves 7 in a base element 8 surrounding the housing 1 and the connector 3

Figure 4:
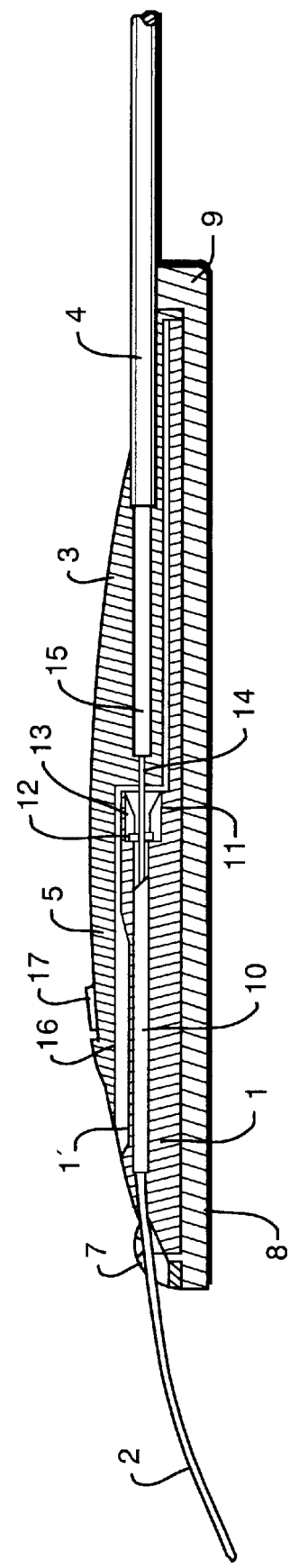
FIG. 4 is a sectional view along the line 4—4 in FIG. 1.

From FIG. 4 it appears that a locking arm 5 on the connector 3 comprises a barb 16 co-operating with a transverse bridge element 17 delimiting an aperture or recees 11 in the housing 1. In order to release the connector 3 the locking arm 5 must be pressed down while the connector 3 is retracted from the housing 1.

A guide means may be used to guide the connector 3 into a correct position in relation to the housing 1. For example, as shown in FIG. 1, the guide means may be comprised of sidewalls 30 on the locking arm 5 and side surfaces 32 on the recess 1'.

Figure 2:
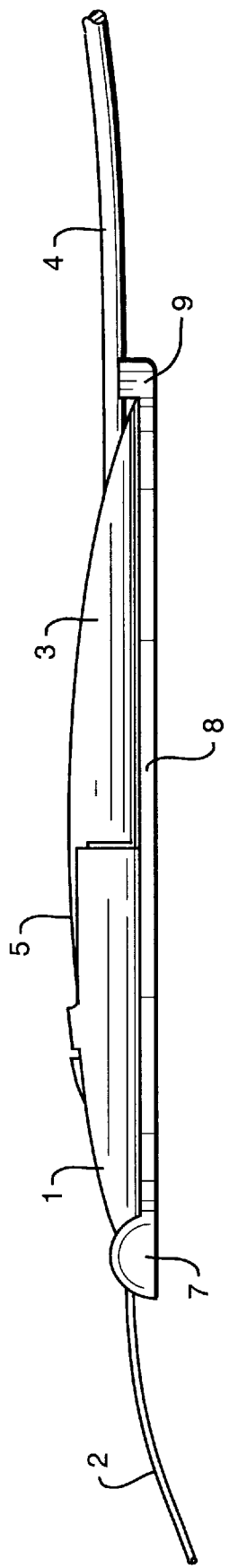
FIG. 2 is a side view of the device shown in FIG. 1.
Figure 3:
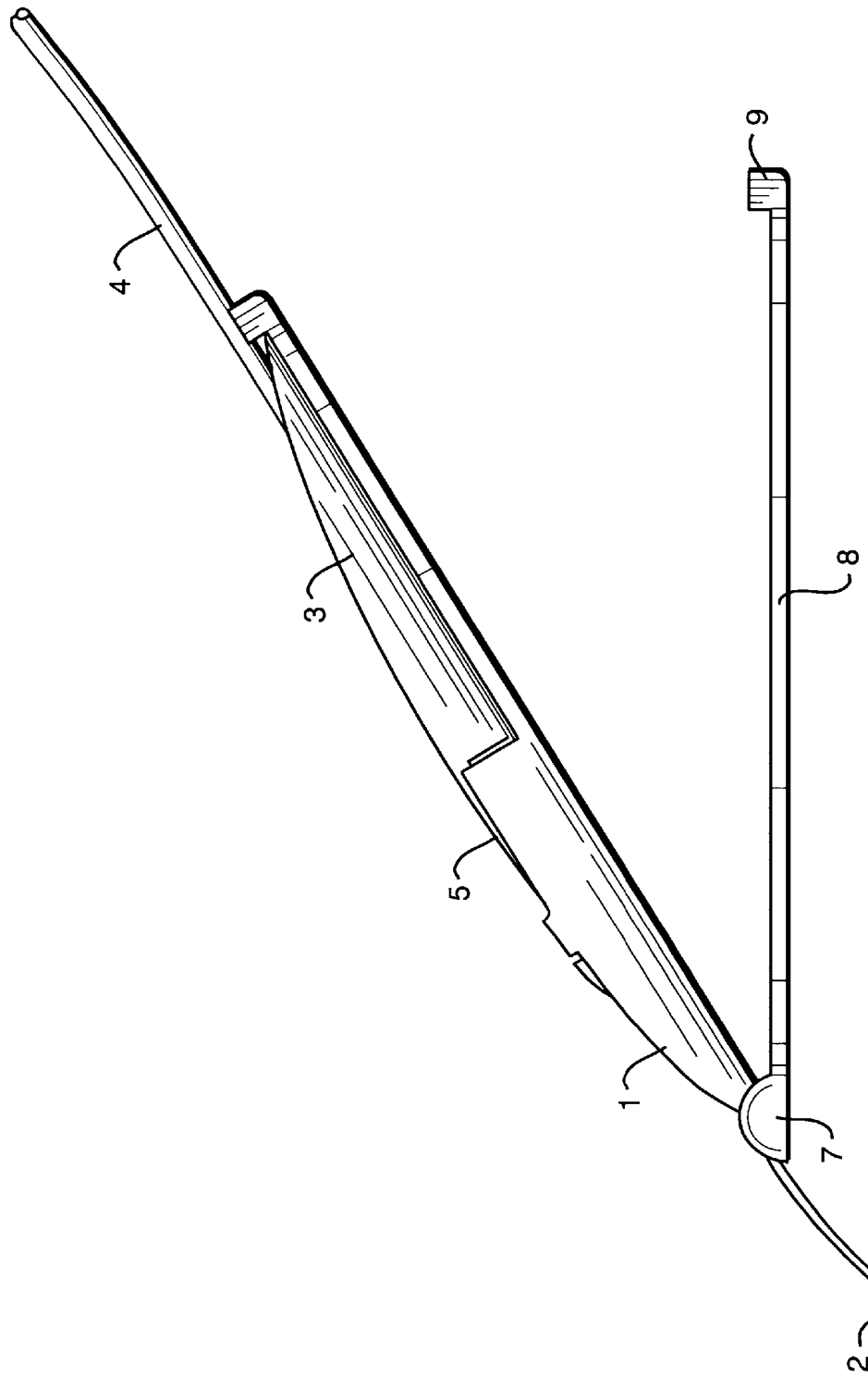
FIG. 3 is a side view of the device shown in FIG. 1 in a pivoted position.

From FIG. 3 the device shown in FIG. 2 appears with the housing and the connector in a position pivoted in relation to the base element 8. Hereby the shafts 6 are pivoted in the grooves 7 of the base element 8. It further appears that the base element provides a locking element for the connector in relation to the housing as the connector is prevented from axial movement due to a protrusion 9 on the base element. Only in a pivoted position, e.g. as shown in FIG. 3, the connector can be released from the housing.

From FIG. 4 it appears that the housing is provided with a bore 10, where at one end of this bore the soft cannula 2 is mounted in flow communication with the bore. At the end 11 of the bore opposite the soft cannula 2 a self-sealing septum 12 is mounted and held in place by means of a holding element 13. The connector comprises a bore 15 where the hose 4 is connected in fluid communication with this bore at one end of this and where at the end of the bore opposite the hose a hollow needle 14 is provided in fluid communication with the bore 15. The needle 14 is provided for penetrating the self-sealing septum 12 in the housing. The self-sealing septum provides a fluid and air seal towards the surroundings when the needle of the connector is retracted from the septum and further provides air and fluid seal around the needle when inserted through the septum.

Figure 5:
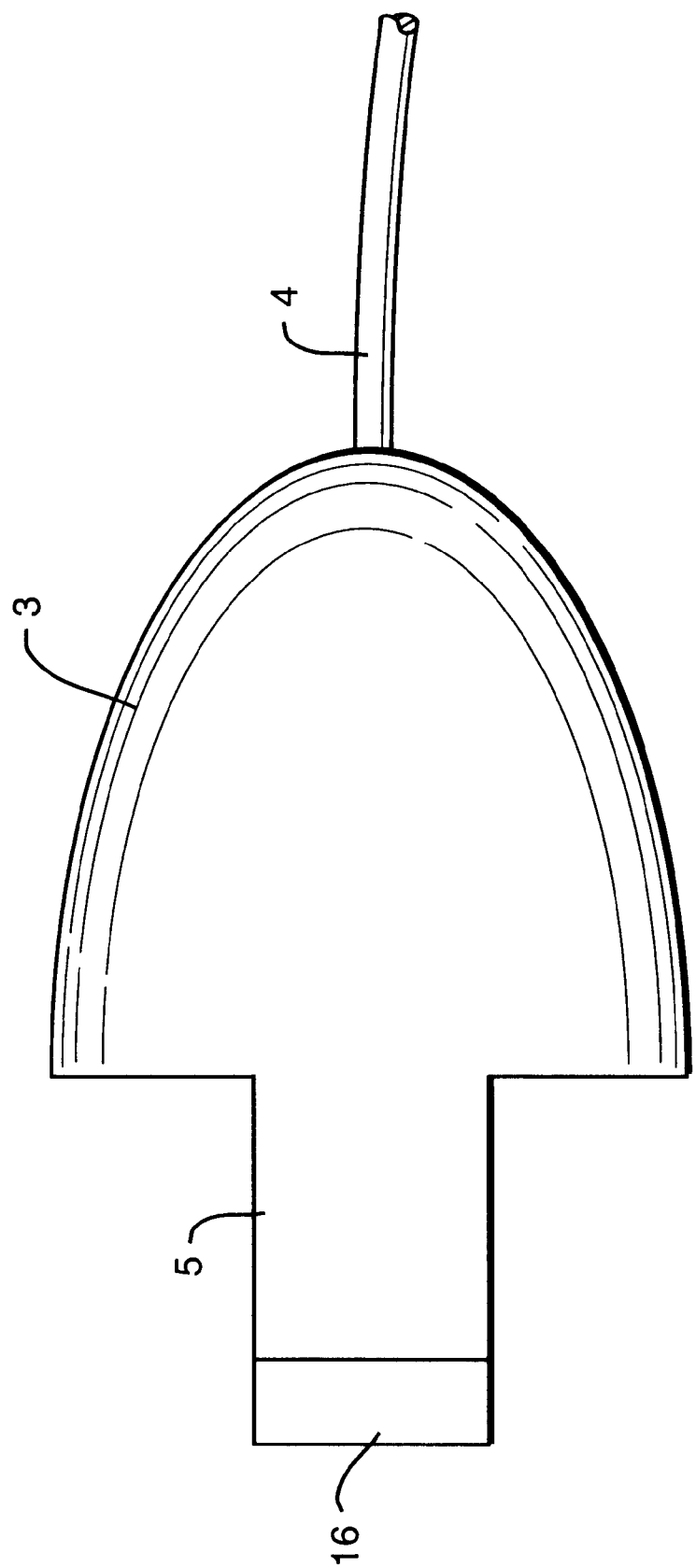
FIG. 5 is a top view of the connector of the device shown in FIG. 1.

From FIG. 5 the connector 3 appears after the release from the housing. It appears that the flexible locking arm 5 extends beyond the needle (not visible), hereby providing a protective shield against harmful injuries caused by the needle.

Figure 6:
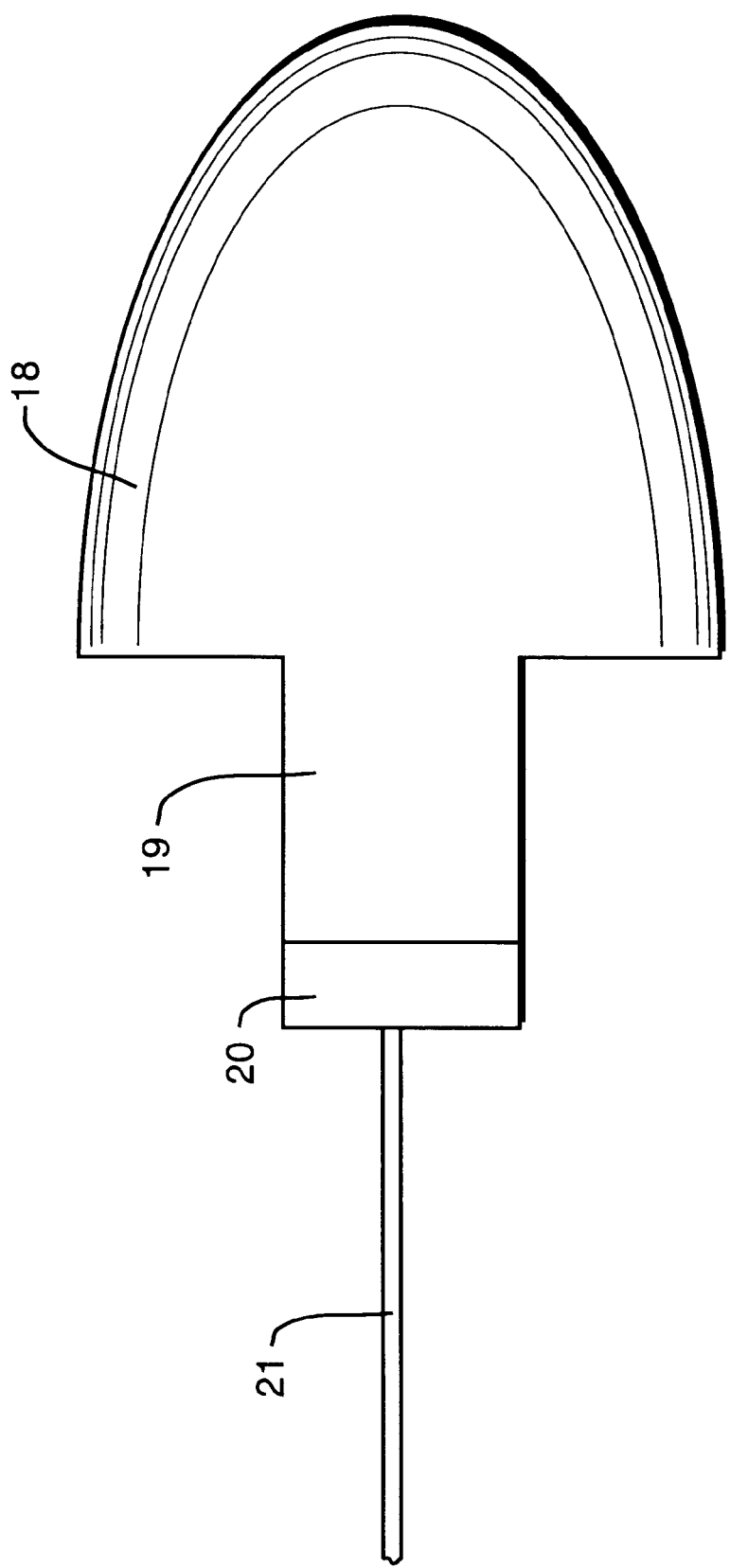
FIG. 6 is a top view of an insertion needle for use in connection with the device shown in FIG. 1.

From FIG. 6 an insertion needle 18 for use in connection with the device shown in FIG. 1 appears. The insertion needle comprises a needle hub 21 adapted to interact with housing in the same manner as the connector, i.e. by means of a single elongate flexible element 19 having a barb 20. The needle extends through the soft cannula beyond the outer tip of this in the insertion position. The insertion needle is removed from the device prior to the connector (3) being attached to the base for fluid communication between the pump (not shown) and the connector.

From FIG. 7 the rear end of the housing appears. The conical entrance for the needle is visualised as well as the groove for the flexible guide and locking arm.

From FIG. 8 the front end of the connector appears. The needle and the flexible guide and locking arm are visualised.

What is claimed is:

1. A subcutaneous infusion device comprising:
   a housing having an internal flow channel;
   a base pivotally interconnected to the housing to allow pivotal movement of said housing with respect to said base between a first position and at least one second position;
   a cannula extending from the housing and being in flow communication with said flow channel;
   a connector having a needle for delivery of fluid into said flow channel, said connector removably connected to said housing;
   guide means arranged on said housing and said connector for guiding the connector with the needle into a correct position in relation to the housing;
   said base including means for preventing disconnection of said connector from said housing with said housing being in said first position.

2. A subcutaneous infusion device as claimed in claim 1, wherein the guide means comprises an elongate flexible element formed on the connector and having a barb, and wherein the housing comprises a recess for receiving the elongate flexible element and locking means adapted for engaging the barb on the elongate flexible element for securing said connector to said housing said device being formed such that the barb may be brought out of engagement with said locking means upon effecting a pressure on the flexible element.

3. A subcutaneous infusion device as claimed in claim 2, wherein the elongate flexible element is placed so as to cover the needle.

4. A subcutaneous infusion device as claimed in claim 1 where a self-sealing septum is provided for covering the flow channel, said needle being adapted for penetrating said self-sealing septum.

5. A subcutaneous infusion device comprising:
   a housing having an internal flow channel;
   a base pivotally interconnected to the housing to allow pivotal movement of said housing with respect to said base between a first position and at least one second position;
   a cannula extending from said housing and being in flow communication with said flow channel;
   a connector having a needle for delivery of fluid into said flow channel, said connector removably connected to the housing;
   a locking element attached to the base for preventing disconnection of said connector from said housing with said housing being in said first position.

6. The subcutaneous infusion device of claim 5, wherein the locking element comprises a protrusion formed integrally with the base.

7. The subcutaneous infusion device of claim 6, wherein the locking element is positioned at a distal end of the base.

8. The subcutaneous infusion device of claim 7, wherein the locking element extends upward from the base in a direction generally perpendicular to the base.

9. The subcutaneous infusion device of claim 8, wherein when the housing is in the first position the locking element is arranged adjacent to a distal end of the housing to prevent the housing from moving in an axial direction.

10. A subcutaneous infusion device, comprising:
    a housing;
    a flow channel within the housing;
    a cannula extending from the housing and being in flow communication with said flow channel;

a connector having a needle for delivery of fluid into said flow channel, said connector removable connected to said housing;

guide means arranged on said housing and said connector for guiding the connector with the needle into a correct position in relation to the housing;

a base part where the housing is mounted pivotably in relation to this base part; and wherein the guide means comprises an elongate flexible element formed on the connector and having a barb, and wherein the housing comprises a recess for receiving the elongate flexible element and a locking means adapted for engaging the barb on the elongate flexible element for securing said connector to said housing said device being formed such that the barb may be brought out of engagement with said locking means upon effecting a pressure on the flexible element.

11. The subcutaneous infusion device of claim 10, wherein the elongate flexible element is placed so as to cover the needle.

12. A subcutaneous infusion device, comprising:

a housing;

a flow channel within the housing;

a cannula extending from the housing and being in flow communication with said flow channel;

a connector having a needle for delivery of fluid into said flow channel, said connector removably connected to said housing;

guide means arranged on said housing and said connector for guiding the connector with the needle into a correct position in relation to the housing;

a base part where the housing is mounted pivotably in relation to this base part; and a self sealing septum is provided for covering the flow channel, said needle being adapted for covering the flow channel, said needle being adapted for penetrating said self-sealing septum.

* * * * *